US006488638B2

(12) United States Patent
Mushabac

(10) Patent No.: US 6,488,638 B2
(45) Date of Patent: Dec. 3, 2002

(54) DENTAL INSTRUMENT ASSEMBLY

(76) Inventor: David R. Mushabac, 919 Ocean Ave., Brooklyn, NY (US) 11226

(*) Notice: Subject to any disclaimer, the term of this patent is extended or adjusted under 35 U.S.C. 154(b) by 11 days.

(21) Appl. No.: 09/811,851

(22) Filed: Mar. 19, 2001

(65) Prior Publication Data
US 2002/0133095 A1 Sep. 19, 2002

(51) Int. Cl.$^7$ .......................... A61B 5/103; A61C 19/04
(52) U.S. Cl. .......................... 600/590; 433/68; 433/215
(58) Field of Search .......................... 600/587, 589, 600/590; 433/201.1, 214, 27, 25, 68; 264/16, 19; 606/53

(56) References Cited

U.S. PATENT DOCUMENTS

| 4,182,312 A | * | 1/1980 | Mushabac | ..................... 264/16 |
| 5,224,049 A | | 6/1993 | Mushabac | |
| 5,257,184 A | | 10/1993 | Mushabac | |
| 5,343,391 A | | 8/1994 | Mushabac | |
| 5,347,454 A | | 9/1994 | Mushabac | |
| 5,359,511 A | * | 10/1994 | Schroeder et al. | ............ 433/75 |
| 5,448,472 A | | 9/1995 | Mushabac | |
| 5,545,039 A | | 8/1996 | Mushabac | |
| 5,562,448 A | | 10/1996 | Mushabac | |
| 5,569,578 A | | 10/1996 | Mushabac | |
| 5,957,868 A | * | 9/1999 | Case et al. | ..................... 33/514 |

* cited by examiner

Primary Examiner—Teresa Walberg
Assistant Examiner—Thor Campbell
(74) Attorney, Agent, or Firm—R. Neil Sudol; William Sapone; Henry Coleman

(57) ABSTRACT

A dental instrument assembly includes a motion-tracking hexapod including a plurality of telescoping members each connected at one end to a first frame and at an opposite end to a second frame and further including a plurality of linear transducers each operatively coupled to a respective one of the telescoping members for generating a signal indicative of a degree of extension of the respective one of the telescoping members. A generally U-shaped bracket is connected to the first frame for mounting the first frame to a row of teeth in a patient's mouth, and a dental instrument or probe is mounted to the second frame. A computer connected to the transducers is connected to other computers via the Internet for enabling dental data exchange.

19 Claims, 2 Drawing Sheets

DENTAL INSTRUMENT ASSEMBLY

BACKGROUND OF THE INVENTION

This invention relates to a motion-tracking instrument assembly. The device may be used in the collection of data geometrically characteristic of or defining a surface. More particularly, the device is connectable to a computer for providing the computer with electrically encoded data derived from and in part specifying a three-dimensional surface or curvilinear contour of an object. Alternatively, the device is utilizable to produce a controlled motion, for instance, of a tool or instrument. The invention is particularly useful in the practice of dentistry.

U.S. Pat. No. 5,569,578 discloses a system for effecting a desired modification in the shape of a pre-existing object to which access is restricted. The system is particularly useful in the practice of dentistry to effect the preparation of a tooth for a filling, a crown or inlay or other restoration. The system of U.S. Pat. No. 5,569,578 includes a computer, a first data generating device, a second data generating device, a display, an instruction input device and an output device. The first data generating device is operatively connected to the computer for providing the computer with electrically encoded data specifying a three-dimensional surface of the object, while the second data generating device is operatively connected to the computer for providing the computer with electrically encoded data specifying a curvilinear contour of the object. The display is responsive to signals from the computer for displaying a three-dimensional graphic representation of the object in accordance with data from the first data generating device and the second data generating device. The instruction input device operatively serves for instructing the computer to modify the three-dimensional representation of the object on the display and for selecting a modification of the three-dimensional representation which represents a desired object preparation. The output device is operatively coupled to the computer for issuing an output signal to effectuate a limitation in motion of a preparation instrument relative to the object so that the object is provided with the desired object preparation.

The first data generating device of U.S. Pat. No. 5,569,578 includes a scanning component for optically scanning the three-dimensional surface of the object and transmitting a video signal of the three-dimensional surface to the computer. More specifically, the first data generating device includes a projection assembly for optically imposing a grid on the object's three-dimensional surface. In using the first data generating device, an operator provides a reference distance at the three dimensional surface being scanned.

The second data generating device of U.S. Pat. No. 5,569,578 includes a manipulable stylus-type instrument having a distal tip engageable with the object and further includes a position detection assembly for monitoring the location of the stylus tip relative to the object and for feeding electrically encoded data regarding the stylus tip location to the computer. In a preferred embodiment of the second data generating means, the position detection assembly comprises what is called here a pantograph assembly that functions to duplicate motion. The assembly includes a pantograph extension rigidly connected to the stylus-type instrument and an optical scanner for tracking the location of a point on the pantograph extension and transmitting a resulting video signal to the computer.

The second data generating device of a shape modification system in accordance with the disclosure of U.S. Pat. No. 5,569,578 enables a dentist or other operator to obtain shape data about areas which are not optically accessible, for example, areas below the gum line of a tooth. Such information is necessary for enabling tooth preparation to extend below the gum line. The shape modification system further comprises a cutting instrument and a position detection assembly for monitoring the location of a tip of the cutting instrument relative to the object and for feeding data regarding the cutting tip location to the computer. The position detection assembly may take the form described above with reference to the stylus-type instrument of the second data generating device, i.e., it may include a pantograph extension connected to the cutting instrument and an optical scanner for optically scanning the location of a point on the pantograph extension and transmitting a resulting video signal to the computer.

As described in U.S. Pat. No. 5,569,578, a cutting tool attachment may be substituted for a stylus attachment on a handle, holder or frame member. Thus, the instruction input device may include a cutting instrument and position detection assembly for monitoring the location of a tip of the cutting instrument relative to the object and for feeding data regarding the location to the computer. The position detection assembly may be of the kind described hereinabove. Using a cutting tool such as a drill enables an operator such as a dentist to feed a desired depth to the computer. The depth is useable by the computer to select and/or calculate a suggested tooth preparation and to show the suggested preparation on the display.

Alternatively or additionally, the instruction input device includes a keyboard connected to the computer and/or a contact sensitive region of the display. In this case, for example, the desired depth of a tooth preparation may be entered numerically. In addition, the operator may inform the computer via the keyboard of the type of tooth preparation which is desired. If a tooth being worked on is to receive a crown, the operator or dentist informs the computer, in one procedure according to the invention, to remove a certain percentage (e.g., 10%) from all top and side surfaces of the tooth to the contour below the gum line defined by the second data generating device.

OBJECTS OF THE INVENTION

An object of the present invention is to provide a motion-tracking device utilizable in an input mode for sensing three-dimensional motion and utilizable alternatively or additionally in an output mode for producing three-dimensional motion.

Another object of the present invention is to provide such a device which generates three-dimensional contour data of an object such as a tooth.

A related object of the present invention is to provide a data-gathering device which incorporates a position detection assembly for monitoring the location of a stylus tip relative to an object and for feeding electrically encoded data regarding the stylus tip location to a computer.

Yet a further object of the present invention is to provide a device which is utilizable in the practice of dentistry to collect in situ information about tooth surfaces.

These and other objects of the present invention will be apparent from the drawings and descriptions hereof. Every object of the invention is attained by at least one embodiment of the present invention. However, not every embodiment will necessarily attain every objective set forth herein.

SUMMARY OF THE INVENTION

A dental instrument assembly comprises, in accordance with the present invention, a first frame, a second frame, a plurality of telescoping members each connected at one end to the first frame and at an opposite end to the second frame, a plurality of linear transducers each operatively coupled to a respective one of the telescoping members for generating a signal indicative of a degree of extension of the respective one of the telescoping members, a generally U-shaped bracket connected to the first frame for mounting the first frame to a row of teeth in a patient's mouth, and a dental instrument or probe mounted to the second frame.

It is contemplated that the linear transducers are operatively connected to a computer programmed to track motion of the dental probe or instrument at least partially in response to signals from the linear transducers.

Pursuant to another feature of the present invention, the dental instrument or probe is detachably mounted to the second frame. More specifically, the dental instrument or probe may be slidably secured to an elongate arm in turn connected to the second frame. Where the elongate arm is connected to the second frame via a rotary joint, the dental instrument assembly further comprises a rotary transducer operatively linked to the rotary joint for generating a signal indicative of a degree of angular displacement of the arm about an axis.

In accordance with a further feature of the present invention, a plurality of independently operable drive elements are operatively connected to the telescoping members for automatically varying degrees of extension of the telescoping members. It is contemplated that the drive elements are connected to a computer for controlling the degrees of extension of the telescoping members. Where the dental instrument or probe is mounted to the second frame via a linkage having a predetermined number of degrees of freedom of motion, the dental instrument assembly may additionally comprise a number of additional drive elements operatively connected to the linkage for automatically varying an operational configuration of the linkage.

A dental instrument assembly comprises, in accordance with another embodiment of the present invention, at least two multipod devices each including a first frame, a second frame, a plurality of telescoping members each connected at one end to the first frame and at an opposite end to the second frame, and a plurality of linear transducers each operatively coupled to a respective one of the telescoping members for generating a signal indicative of a degree of extension of the respective one of the telescoping members. The instrument assembly of this other embodiment of the present invention further comprises a generally U-shaped bracket connected to the second frame of one of the multipod devices for mounting that second frame to a row of teeth in a patient's mouth. A dental instrument or probe is mounted to the second frame of another of the multipod devices. The first frames of the multipod devices are at least indirectly mounted to a stationary fixture and thus at least indirectly connected to each other.

A numerically controllable tool assembly comprises, in accordance with a further embodiment of the present invention, a first frame, a second frame, a plurality of telescoping members each connected at one end to the first frame and at an opposite end to the second frame, a plurality of drive elements each operatively coupled to a respective one of the telescoping members for automatically varying a degree of extension of the respective one of the telescoping members, a bracket connected to the first frame for mounting the first frame to an object, and a tool or operating instrument mounted to the second frame. The drive elements are connected to a computer for controlling the degrees of extension of the telescoping members. Where the tool or operating instrument is mounted to the second frame via a linkage having a predetermined number of degrees of freedom of motion, the numerically controllable tool assembly also comprises a number of additional drive elements operatively connected to the linkage for automatically varying an operational configuration of the linkage.

DETAILED DESCRIPTION OF THE DRAWINGS AND OF THE PREFERRED EMBODIMENTS

Figure 1:
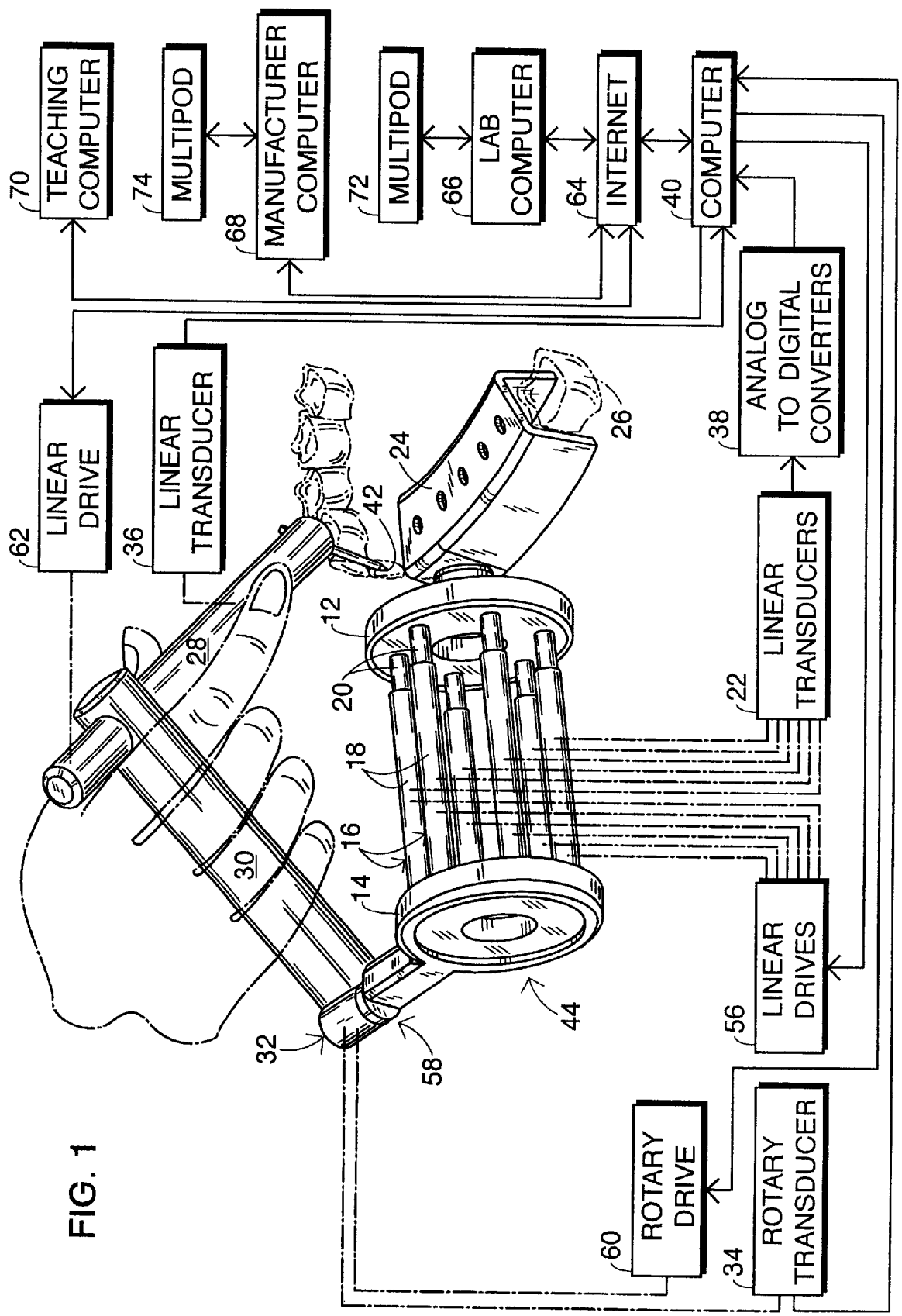
FIG. 1 is partially a block diagram and partially a schematic perspective view of a dental system incorporating a dental instrument assembly in accordance with the present invention.

As illustrated in FIG. 1, a dental instrument assembly comprises an annular first frame 12, an annular second frame 14, and a plurality of telescoping members 16 each having an outer tube 18 and an inner tube 20 slidably inserted inside the outer tube. At ends opposite outer tubes 18, inner tubes 20 are pivotably connected to frame 12, preferably via universal joints (not shown). Concomitantly, at ends opposite inner tubes 20, outer tubes 18 are pivotably connected to frame 14, also preferably via universal joints (not shown). A plurality of linear transducers 22 are operatively coupled to respective ones of the telescoping members 16 for generating respective signals indicative of degrees of extension of the respective telescoping members 16.

As further illustrated in FIG. 11, an arcuate generally U-shaped bracket 24 is rigidly connected to frame 12 for fixing that frame to a row of teeth 26 in a patient's mouth (not shown). A dental instrument or probe 28 is movably mounted to frame 14 via an elongate arm 30 and a rotary joint 32. A rotary transducer 34 is operatively linked to joint 32 for generating a signal encoding a degree of angular displacement of arm 30 about an axis (not shown) extending perpendicularly to arm 30 and through frame or plate 14.

Dental instrument 28 is preferably removably attached to an end of arm 30 opposite rotary joint 32. However, it is possible for dental instrument 28 to be movably coupled to arm 30 so that the position of the dental instrument relative to arm 30 can change during use. In that case, an additional linear transducer 36 is mounted to arm 30 in operatively communication with arm 30 for measuring the degree of shifting of the dental instrument.

Linear transducers 22 and 36 are connected via analog-to-digital converters 38 to a computer 40 programmed to track motion of dental instrument 28 at least partially in response to signals from transducers 22 and 36, as well as a signal from rotary transducer 34. Transducer 34 may be provided with an analog-to-digital converter (not shown) for providing a digital input to computer 40.

Dental instrument 28 is detachably mounted to frame 14 to enable the replacement of the dental instrument with a different instrument depending on a task to be performed. The positioning of the various instruments may be predetermined and/or communicated to computer 40 during a calibration step, so that computer 40 is able to track the location of an operative tip 42 of whatever instrument is mounted to arm 30.

Frames 12 and 14 together with telescoping members 16 and linear transducers 22 are known in the art as a hexapod 44 inasmuch as telescoping members 16 are six in number. Generally, six telescoping members 16 and transducers 22 provide sufficient data to a motion-tracking computer to entirely specify six degrees of freedom of an element rigidly secured to one of the frame members 12 and 14. However, it is recognized that fewer or more telescoping members 16 may be used. Fewer telescoping members 16 may be present where additional encoders or motion-detecting transducers (e.g., transducers 34 and 36) generate motion-tracking data. Accordingly, the coined term "multipod" is used herein to generically represent motion-tracking devices with a plurality of telescoping members between two frames.

The instrument assembly shown in FIG. 1 may be used as described in U.S. Pat. Nos. 5,569,578, 5,224,049, 5,347,454, 5,545,039, 5,562,448, and 5,343,391 to enable the input of three-dimensional and surface contour information into computer 40. In particular, dental instrument 28 may be manipulated by a dental practitioner to trace a contour of a tooth below the gum line or in between adjacent teeth, with the motion of tip 42 being tracked via telescoping arms 16 and transducers 22 and provided in encoded format to computer 40. The uses of the information for diagnostic and therapeutic purposes are described in those prior patents, the disclosures of which are hereby incorporated by reference.

Figure 2:
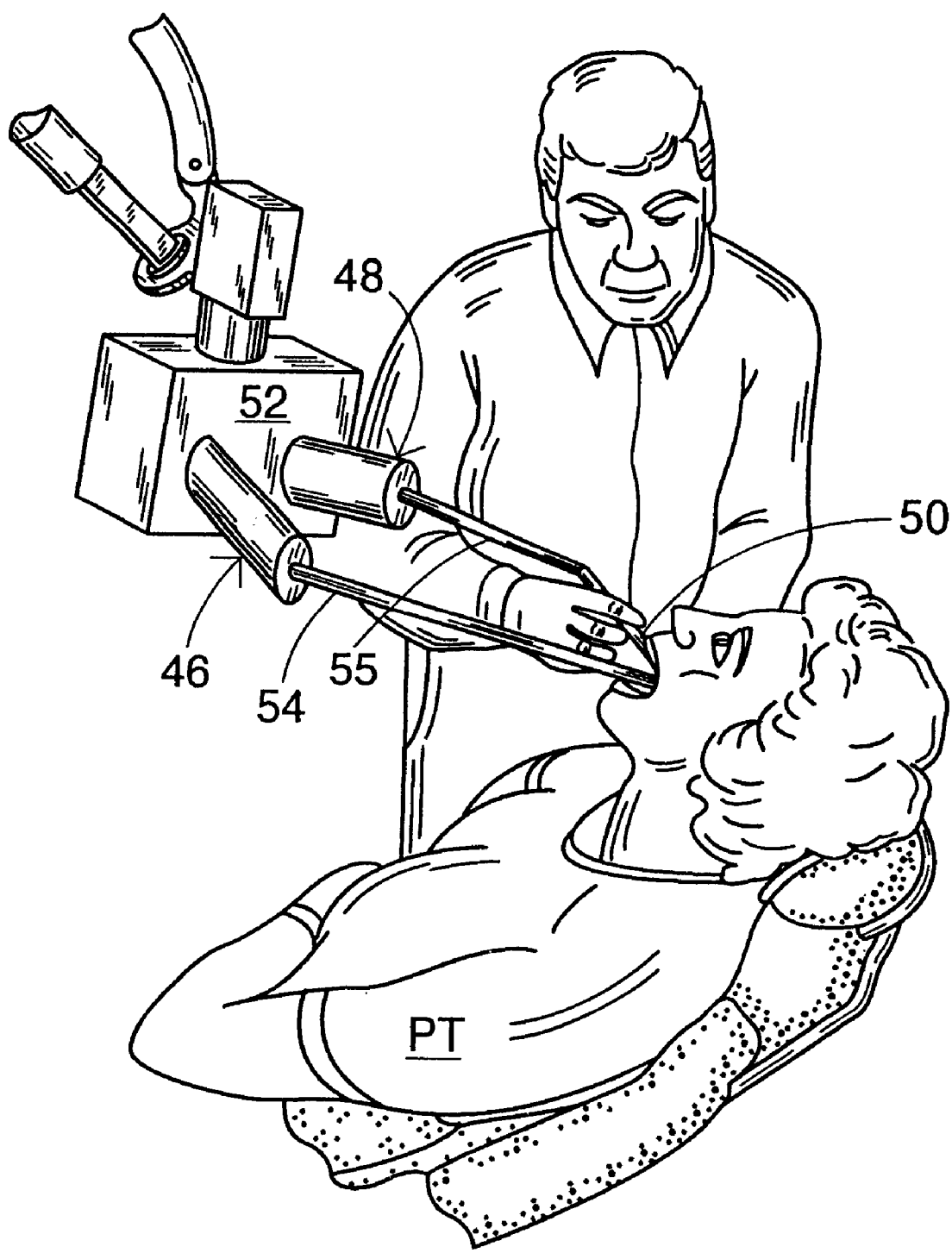
FIG. 2 is a schematic perspective view of an alternative dental instrument assembly in accordance with the present invention.

As illustrated in FIG. 2, a plurality of multipods 46 and 48 may be used to track the motion of a dental probe 50 relative to a patient PT and particularly relative to tooth surface in the patient's mouth. Multipods 46 and 48 may take the form of hexapod 44 shown in FIG. 1. Multipods 46 and 48 each have a first frame (see reference designations 12, 14 in FIG. 1) connected to a fixture 52 in the dental office. A second frame (14, 12, FIG. 1) of multipod 46 is fixedly secured connected to a jaw of the patient PT via an arm 54 and a U-shaped bracket 24 (FIG. 1). A second frame (14, 12, FIG. 1) of multipod 48 is connected to dental probe 50 via a linkage 55 as discussed above with reference to dental instrument 28, arm 30, and rotary joint 32. As described in the above-listed patents, particularly U.S. Pat. No. 5,343, 391, the multipod arrangement of FIG. 2 allows a controlled feeding of surface and contour information to computer 40 (FIG. 1) for diagnostic and therapeutic purposes.

As additionally depicted in FIG. 1, a plurality of independently operable linear drive elements 56 are operatively connected to telescoping members 16 and to computer 40 for automatically varying degrees of extension of the telescoping members in response to control signals from computer 40. Where dental instrument 28 is mounted to frame 14 via a linkage 58 having a predetermined number of degrees of freedom of motion, the dental instrument assembly may additionally comprise a like number of additional drive elements 60 and 62 operatively connected to the linkage and to computer 40 for automatically varying an operational configuration of the linkage in response to signals from computer 40.

As described in U.S. Pat. Nos. 5,569,578, 5,224,049, 5,347,454, 5,545,039, 5,562,448, and 5,343,391, the motorization of hexapod 44 and linkage 58 enables computer 40 to move dental instrument 28 and particularly operative tip 42 along a predetermined path pursuant to numerical control principles.

As further illustrated in FIG. 1, computer 40 is connected to the global computer network 64 known as the Internet for communicating over that network with other computers in the dental industry including a laboratory computer 66, a manufacturer's computer 68, and a teaching computer 70. Computer 40 is able to share dental data pertaining to an individual patient with computers 66, 68, and 70. Lab computer 66 and manufacturer computer 68 are operatively connected to respective multipods 72 and 74 for enabling an input of surface and contour data at the locations of the laboratory and manufacturer. Teaching computer 70 may also have a dedicated multipod (not shown) for facilitating the execution of heuristic pursuits.

The transfer or "shipping" of important patient data, from a dental practitioner's site to supporting resources such as a dental lab or to another practitioner as a specialist, is in one sense a customary mode of standard operations. Impressions, models, are sent to labs, worked on there and returned to their originating office, with finished restorations, and/or as dental replacements, such as bridges, dentures, etc. However, in utilization of an instrument system as illustrated in FIG. 1, the transfer of models, impressions, and other information via Internet-mediating conferencing may be considered as a modernized/avante garde technology utilizing all the present day advances in computers, optics, and engineering with mechanics for referencing positions and motion sensing. This strategic interactivity is accompanied by a sensing on-line and display of data. The visualization of displays are at multiple sites and are accessible by duplicated instrument-sensors for such interactive capabilities. A dental system as shown in FIG. 1 accommodates a full range of designs, means and methods, along with an in-depth hierarchy of instruments which can be used with software programs. With the program operations are linkages and networking to multi-site locations of practitioner/consulting specialists, and other production-assisting people. Further, conventional tools and instruments may be incorporated into the dental system of FIG. 1 for purposes that include procedure demonstrations (dental/surgical) and tutorials and information transfers. These include on-line probe visualizations overlaid into pictures and graphics, along with interactive participation of practitioners and technicians, specialists, instructors, and other involved professionals with responsive to and with knowledge sought for in enabling and improvement of diagnosis and treatments.

The sharing of dental data among computers 40, 66, 68, and 70 in FIG. 1 may be for various purposes and usages disclosed in U.S. Pat. Nos. 5,569,578, 5,224,049, 5,347,454, 5,545,039, 5,562,448, and 5,343,391. The system of FIG. 1 facilitates and enables, among other things, a generation of electronic models of dental restorations and prostheses via near instantaneous information transfer. The electronic models and prostheses can be used in guiding practitioners in their daily work. In addition, the electronic models and prostheses can be used in numerically controlled processes to actually produce crowns, fillings, bridges, implants and other dental appliances on a customized basis.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A dental instrument assembly comprising:
    a first frame;
    a second frame;
    a plurality of telescoping members each connected at one end to said first frame and at an opposite end to said second frame;

a plurality of linear transducers each operatively coupled to a respective one of said telescoping members for generating a signal indicative of a degree of extension of the respective one of said telescoping members;

a generally U-shaped bracket connected to said first frame for mounting said first frame to a row of teeth in a patient's mouth; and a dental instrument or probe mounted to said second frame.

2. The assembly defined in claim 1 wherein said dental instrument or probe is detachably mounted to said second frame.

3. The assembly defined in claim 2 wherein said dental instrument or probe is slidably secured to an elongate arm in turn connected to said second frame.

4. The assembly defined in claim 3 wherein said elongate arm is connected to said second frame via a rotary joint, further comprising a rotary transducer operatively linked to said rotary joint for generating a signal indicative of a degree of angular displacement of said arm about an axis.

5. The assembly defined in claim 1 wherein said dental instrument or probe is secured to an elongate arm in turn connected to said second frame.

6. The assembly defined in claim 5 wherein said elongate arm is connected to said second frame via a rotary joint, further comprising a rotary transducer operatively linked to said rotary joint for generating a signal indicative of a degree of angular displacement of said arm about an axis.

7. The assembly defined in claim 1, further comprising a plurality of independently operable drive elements operatively connected to said telescoping members for automatically varying degrees of extension of said telescoping members.

8. The assembly defined in claim 7 wherein said drive elements are connected to a computer for controlling the degrees of extension of said telescoping members.

9. The assembly defined in claim 8 wherein said dental instrument or probe is mounted to said second frame via a linkage having a predetermined number of degrees of freedom of motion, also comprising a number of additional drive elements operatively connected to said linkage for automatically varying an operational configuration of said linkage.

10. The assembly defined in claim 1 wherein said linear transducers are operatively connected to a computer programmed to track motion of said dental probe or instrument at least partially in response to signals from said linear transducers.

11. A dental instrument assembly comprising:

(a) at least two multipod devices each including:
 a first frame;
 a second frame;
 a plurality of telescoping members each connected at one end to said first frame and at an opposite end to said second frame; and
 a plurality of linear transducers each operatively coupled to a respective one of said telescoping members for generating a signal indicative of a degree of extension of the respective one of said telescoping members;

(b) a generally U-shaped bracket connected to the second frame of one of said multipod devices for mounting the second frame of said one of said multipod devices to a row of teeth in a patient's mouth; and (c) a dental instrument or probe mounted to the second frame of another of said multipod devices,
 the first frame of said one of said multipod devices and the first frame of said another of said multipod devices being at least indirectly mounted to a stationary fixture and thus at least indirectly connected to each other.

12. The assembly defined in claim 11 wherein said dental instrument or probe is secured to an elongate arm in turn connected to the second frame of said another of said multipod devices.

13. The assembly defined in claim 12 wherein said elongate arm is connected to the second frame of said another of said multipod devices via a rotary joint, further comprising a rotary transducer operatively linked to said rotary joint for generating a signal indicative of a degree of angular displacement of said arm about an axis.

14. The assembly defined in claim 11 wherein said dental instrument or probe is detachably mounted to the second frame of said another of said multipod devices.

15. The assembly defined in claim 11, further comprising a plurality of independently operable drive elements operatively connected to telescoping members of said another of said multipod devices for automatically varying degrees of extension of the telescoping members of said another of said multipod devices.

16. The assembly defined in claim 11 wherein said linear transducers are operatively connected to a computer programmed to track motion of said dental probe or instrument at least partially in response to signals from said linear transducers.

17. A numerically controllable tool assembly comprising:
 a first frame;
 a second frame;
 a plurality of telescoping members each connected at one end to said first frame and at an opposite end to said second frame;
 a plurality of drive elements each operatively coupled to a respective one of said telescoping members for automatically varying a degree of extension of the respective one of said telescoping members;
 a bracket connected to said first frame for mounting said first frame to an object; and
 a tool or operating instrument mounted to said second frame.

18. The assembly defined in claim 17 wherein said drive elements are connected to a computer for controlling the degrees of extension of said telescoping members.

19. The assembly defined in claim 18 wherein said tool or operating instrument is mounted to said second frame via a linkage having a predetermined number of degrees of freedom of motion, also comprising a number of additional drive elements operatively connected to said linkage for automatically varying an operational configuration of said linkage.

* * * * *